United States Patent [19]
Itoh et al.

[11] Patent Number: 5,180,672
[45] Date of Patent: Jan. 19, 1993

[54] ASCORBATE OXIDASE ISOLATED FROM ACREMONIUM SP. HI-25 FERM BP-3124

[75] Inventors: Homare Itoh, Aichi; Takashi Shin, Hyogo; Takahisa Yajima; Shigeki Fukuyasu, both of Aichi, all of Japan

[73] Assignee: Asahi Kasei Kogyo Kabushiki Kaisha, Osaka, Japan

[21] Appl. No.: 653,709

[22] Filed: Feb. 6, 1991

[30] Foreign Application Priority Data

Feb. 13, 1990 [JP] Japan .................................. 2-32175

[51] Int. Cl.$^5$ ........................ C12N 9/04; C12N 1/12; C12N 1/00
[52] U.S. Cl. .................................. 435/190; 435/822; 435/252.1
[58] Field of Search ............ 435/189, 190, 822, 252.1

[56] References Cited

FOREIGN PATENT DOCUMENTS

| 442781A2 | 8/1991 | European Pat. Off. ............ 435/189 |
| 3108485 | 5/1991 | Japan ................................... 435/189 |
| 2066264 | 6/1981 | United Kingdom ................ 435/189 |

OTHER PUBLICATIONS

Men Hui Lee & Charles R. Dawson, J. Biol. Chem., vol. 248, No. 19, 6596–6602.
Enzymes Handbook (Asakura Shobou)–p. 156.
T. Nakamura, N. Makino & Y. Ogura, Biochem. J. vol. 64, No. 2, 189–195, 1968.
Funaki et la., Nihon Eiyou-Shokuryou Gakukaishi, vol. 40, No. 1, 47–51, 1987.
Jean Dayan & Charles R. Dawson, Bio-chemical & Biophysical Research Communication, vol. 73, No. 2, 451–458, 1976.
Marchesini Patent Publication No. FR 2,241,260, Mar. 21, 1975.
Chemical Abstracts 99: 4087, 1983.

Primary Examiner—David M. Naff
Assistant Examiner—Mike Meller
Attorney, Agent, or Firm—Darby & Darby

[57] ABSTRACT

An ascorbate oxidase having an optimum pH range of 3.5–4.5 is isolated from Acremonium sp. Hi-25 BP-3124. The ascorbate oxidase is used in foods or drinks to oxidize ascorbate to prevent damage to the foods or drinks by oxidation.

1 Claim, 5 Drawing Sheets

ASCORBATE OXIDASE ISOLATED FROM ACREMONIUM SP. HI-25 FERM BP-3124

The present invention relates to a method for preventing the oxidative deterioration of foods and drinks, taking in advantage of the consumption of oxygen through reaction of an ascorbate-oxidase with its substrates, to a deoxygenating agent used for that purpose, to a novel ascorbate oxidase useful for that purpose, and a method for producing the same.

It has been well known that the oxidative deterioration of foods and drinks is caused by oxygen. To prevent the oxidative deterioration, a method has been known in which oxygen in foods and drinks is eliminated with an inorganic iron agent. This method, however, involves some limitations and difficulties, due to the fact that such inorganic iron agents are non-edible materials.

There has been a method in which an oxygen-consuming enzyme, such as glucose oxidase and alcohol oxidase, is used as the deoxygenating agent, instead of the inorganic iron agent. This method, however, has some difficulties that hazardous hydrogen peroxide is formed during the course of the reaction with the substrate, and it contaminates foods and drinks.

The present invention provides a method for preventing the oxidative deterioration of foods and drinks by using an ascorbate-oxidase as the oxygen-consuming enzyme, which is free from such difficulties, because the reaction of the ascorbate-oxidase with its substrates according to this method forms water, not hydrogen peroxide.

Now, it has been known that ascorbate oxidases, a kind of ascorbic acid-oxidizing enzymes, work as follows:

$$\text{L-ascorbate} + \tfrac{1}{2} O_2 \rightarrow \text{dehydroascorbate} + H_2O$$

and distribute in various plants [Enzymes Handbook (Asakura Shobou), pages 158–159], and are isolated from pumpkin [Men Hui Lee and Charles R. Dawson, J. Biol. Chem., Vol. 248, No. 19, 6596–6602, 1973; and Jean Dayan and Charles R. Dawson, Biochemical and Biophysical Research Communication, Vol. 73, No. 2, 451–458, 1976] and cucumber [T. Nakamura, N. Makino and Y. Ogura, J. Biol. Chem., Vol. 64, No. 2, 189–195, 1968]. However, these ascorbate oxidases originated from plants hardly work in acidic range, therefore, they are not appropriately used for preventing the oxidative deterioration of acidic foods and drinks, such as fruit juice drinks. Also, it is not easy to obtain enzymes from plants inexpensively in a large amount.

As ascorbate oxidases originated from microorganisms, there have been known those originated from the hypha of *Myrothecium verrucaria* and from *Aerobacter aerogenes* [Funaki et al, Nihon Eiyou-Shokuryou Gakukaishi, Vol. 40, No. 1, 47–51, 1987].

The present invention is to provide a novel method for preventing the oxidative deterioration of foods and drinks by using an ascorbateoxidase as the oxygen-consuming enzyme, and a deoxygenating agent used for that purpose. Further, it is to provide a novel ascorbate oxidase particularly useful for that purpose, and a method for producing the same.

In order to dissolve such problems, the present invention is to provide an ascorbate oxidase having at least a substrate specificity against ascorbates and performing a catalytic action of $$\text{ascorbate} + \tfrac{1}{2} O_2 \rightarrow \text{dehydroascorbate} + H_2O$$

and having the following properties:

(1) optimum acting pH of 3.5–4.5;
(2) being activated by $Fe^{++}$ and inhibited by $Cu^{++}$;
(3) molecular weight: $85,000 \pm 5,000$ of molecular weight according to gel filtration method, and $23,000 \pm 2,000$ of molecular weight subunit according to sodium dodecyl sulfate/polyacrylamide gel electrophoresis method;
(4) isoelectric point: pI 4.0 as measured by isoelectric focusing method;
(5) temperature stability: showing the stable activity at not higher than 60° C. at pH 8.0 for 30 minutes; and
(6) pH stability: showing the stable activity at 4° C. within the range of pH 4–11.

Furthermore, the present invention is to provide a method for producing an ascorbate oxidase, characterized by growing a microorganism which belongs to genus Acremonium and has the capability of producing ascorbate oxidase and recovering the ascorbate oxidase from the culture medium.

The present invention is also to provide a method for preventing the oxidative deterioration of foods and drinks, characterized by adding, to food or drink, an ascorbate-oxidase with or without its substrates, thereby to effect deoxygenation of food or drink and to prevent the food or drink from oxidative deterioration thereof.

The present invention is also to provide a method for preventing the oxidative deterioration of foods and drinks, characterized by filling, into a sealed vessel, a food or drink, and an ascorbate-oxidase with its substrates, in such a way that the enzyme and the substrates do not directly contact each other.

The present invention is further to provide a deoxygenating agent characterized by that an ascorbate oxidase and its substrates are contained in a vessel which has an opening, or is at least partially constructed with a gas permeable material, in such a way that the enzyme and the substrates do not react each other before use.

Novel ascorbate oxidase

Producing strain

To obtain microorganisms producing ascorbate oxidase having a lower optimum pH, stored strains, as well as thousands of strains isolated from natural fields, were searched, and consequently one strain was found, which produced an ascorbate oxidase having the optimum pH at approximately pH 4.

According to the consigned test report for the identification of microorganisms of the Institute of Physical and Chemical Research, it is identified to be a microorganism of the genus Acremonium Link, belonging to the class Hyphomycetes in the subdivision Deuteromycotina. Thus, the growing properties of the present strain are as follows:

Growing state on each culture medium after incubation at 30° C. for 14 days:

potato dextrose agar medium a. Growth; slow, 6.0 cm diameter.
b. Surface; dense colony, forming white, short villus aerial hypha. Radial furrows at the center, forming cleistothecium-like conidiomate little ratedly. Occasionally forming light brown moisture drops at the surface.
c. Reverse; wrinkles, cream color.
d. Pigment; absent.

Sabouraud's agar medium a. Growth; slow, 5 6 cm diameter.
b. Surface; white, short villi, forming radial furrows with a slight unheaval at the center.
c. Reverse; wrinkles, lemon color.
d. Pigment; absent.

malt extract agar medium a. Growth; slow, 5.1 cm diameter.
b. Surface; white, short villi, forming radial furrows around the center.
c. Reverse; wrinkles, yellowish brown.
d. Pigment; absent.

YpSs agar medium a. Growth; slow, 6.0 cm diameter.
b. Surface; flat, white, short villus aerial hypha. Forming cleistothecium-like conidiomate little ratedly. Occasionally forming light brown moisture drops at the surface.
c. Reverse; no wrinkle, cream color.
d. Pigment; absent.

Physiological properties; growing conditions on a potato dextrose medium are as follows:

optimum growing conditions

Optimum temperature; 28°-31° C.
Optimum growing pH; 6.0-7.0 growing ranges

Growing temperature range; 15°-35° C.
Growing pH range; 5.0-7.8

Optical microscopic observations of the present strain are as follows: Phialides and phialoconidia are formed. The phialides have almost no branching and gradually tapering collula with obscure collar. The phialoconidia are colorless, smooth, unicellular, spherical-subspherical (rarely ellipsoidal-ovoid), with diameter of 1.5-2 (to 4) μm, forming viscous mass. Cleistothecium-like conidiomata formed somewhat ratedly looks like sporodochia which genus Agyriella forms. The conidiomata are white, subspherical-ellipsoidal, with not more than 1 mm diameter, but recognized with the naked eye. They are bulk of naked conidia not embraced with hyphal wall etc., and have phialides formed on top of the branched hypha inside. Each phialide is in the shape of flask, subspherical at its base, and extremely tapered off at the top, often curved. The phialoconidia can not be discriminated morphologically with those of Acremonium synanamorph, but they are viscous mass, much prolific, accumulated among branched hypha. Thus, the present strain is named Acremonium sp, HI-25.

The present Acremonium strain has been deposited at the Fermentation Research Institute, Agency of Industrial Science and Technology, Chiba, Japan, bearing deposition number of FERM P-11236, which was tranferred to FERM BP-3124 on Jan. 29, 1990.

The strain to be employed for the production of the ascorbate oxidase of the present invention is not limited to that mentioned above, but any of its variant strains, and other strains producing the enzyme of the present invention may of course be employed.

Cultivation

Any cultivating method may be employed for the cultivation of the Acremonium strain to produce the ascorbate oxidase. For example, liquid culture method is mentioned as follows. Any culture medium may be employed so far as it allows to grow microorganisms belonging to the genus Acremonium and producing the ascorbate oxidase. For example, conventional media for cultivation of fungi and actinomycetes may be employed. For example, a mixture of a carbon source, such as glucose, sucrose, glycerol, dextrin, molasses, organic acids, etc. and at least one member selected, for example, from amino acids, vitamins, yeast extracts, meat extracts, koji extracts, polypeptone, protein hydrolyzates, etc., with or without one or more of inorganic salts, such as salts of potassium, magnesium, sodium, phosphates, manganese, iron, zinc, copper, etc., is suitably used. Starting pH is adjusted, for example, to about 3.5-9.0, preferably about 5.5-6.5. Cultivation is effected generally at a temperature of 15°-42° C., preferably at about 25°-35° C. for 1-20 days, preferably for about 3-12 days, preferably under aerobic condition, for example, by shaken culture or aerobic submerged culture using jar fermenters.

Purification method

Then, the resulting cultivated medium is filtered to remove mycelia, thereby to obtain a culture filtrate. To separate mycelia from cultivated media, any method can be used, for example, a method using conventional centrifuge or filtration. From the culture filtrate thus obtained, the ascorbate oxidase of the invention is isolated and then purified, for example, by any of ammonium sulfate fractionation, alcohol fractionation, DEAE-cellulose treatment, Sephacryl treatment, Sephadex treatment, TSK gel DEAE column treatment, etc., or a combination of these treatments, as required. If necessary, dehydration or drying process is conducted to gain the objective enzyme.

Measurement of enzyme activities

Method of measurement for the activities of the novel ascorbate oxidase of the invention is set forth below. One ml portion of 0.1M sodium acetate buffer solution (pH 4.0) containing 0.5 mM ascorbic acid and 0.5 mM disodium ethylenediaminetetraacetate is preliminarily incubated at 30° C. for 5 minutes. Then, 0.1 ml of an enzyme liquor sample to be tested is added thereto, and the mixture is allowed to react at 30° C. for 5 minutes. After adding 3 ml of 0.2M hydrochloric acid as reaction stopper, an absorbance at 245 nm is measured. The activity is calculated from the difference values of the absorbance at 245 nm of the unaltered mixture.

One unit means the amount of enzyme which oxidizes one $\mu$ mol of ascorbic acid during 1 minute under the enzyme activity measurement conditions Enzyme properties Properties of the ascorbate oxidase produced by Acremonium sp. HI-25 are set forth below.

(1) Optimum pH

Figure 1:
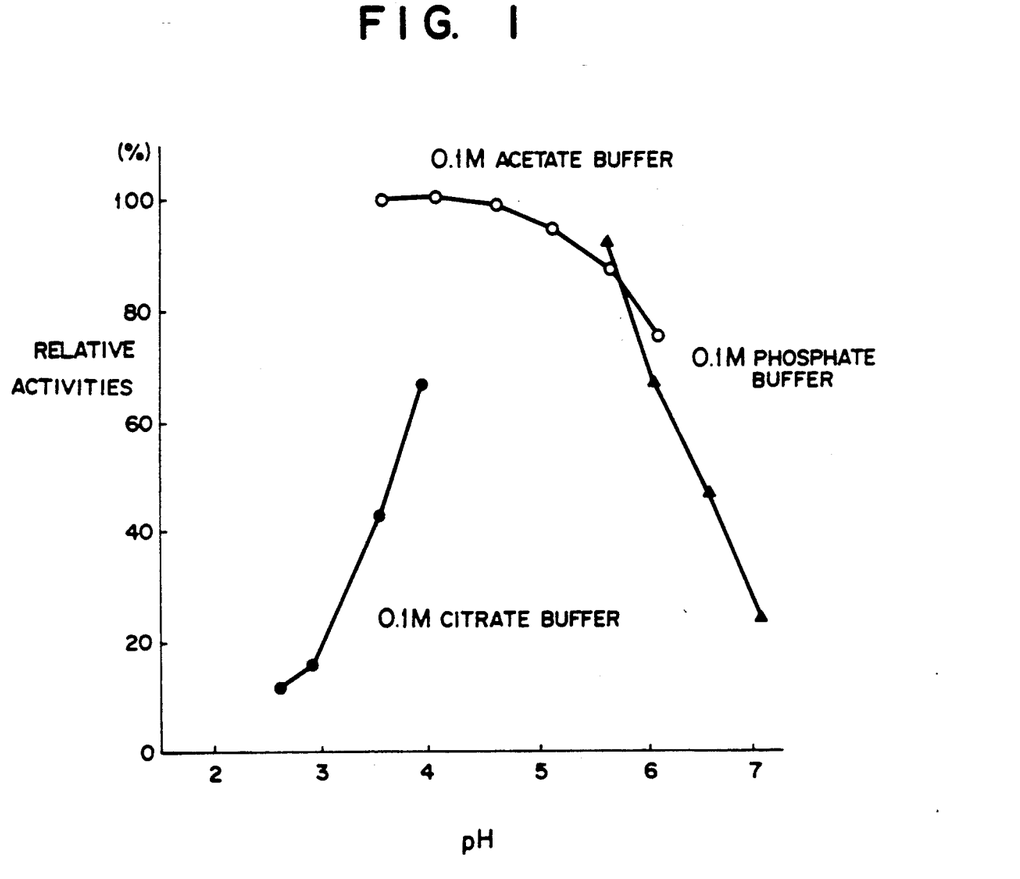
FIG. 1 is a graphic chart showing the optimum acting pH of the ascorbate oxidase produced by Acremonium sp. HI-25.

Reaction at 30° C. for 5 minutes using various kinds of buffer solutions within the range of pH 2.6 — 7.0 gave the results as shown in FIG. 1. Thus, the enzyme of the present invention has the optimum acting pH of 3.5-4.5.

(2) pH stability

Figure 2:
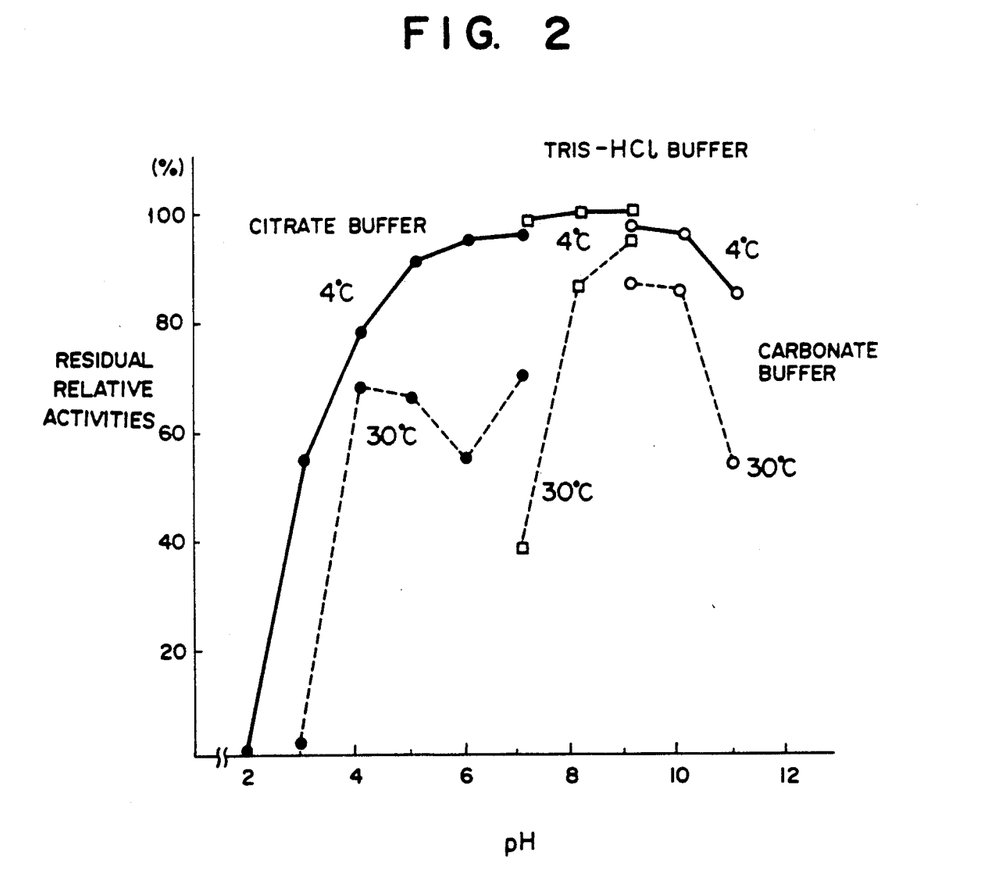
FIG. 2 is a graphic chart showing the pH stability of that enzyme.

Remaining relative activity after incubation of the enzyme at 30° C. or 4° C. for 17 hours at various pH values gave the results as shown in FIG. 2. Thus, the enzyme are stable within the range of pH 4°-11 at 4° C.

(3) Optimum acting temperature

Figure 3:
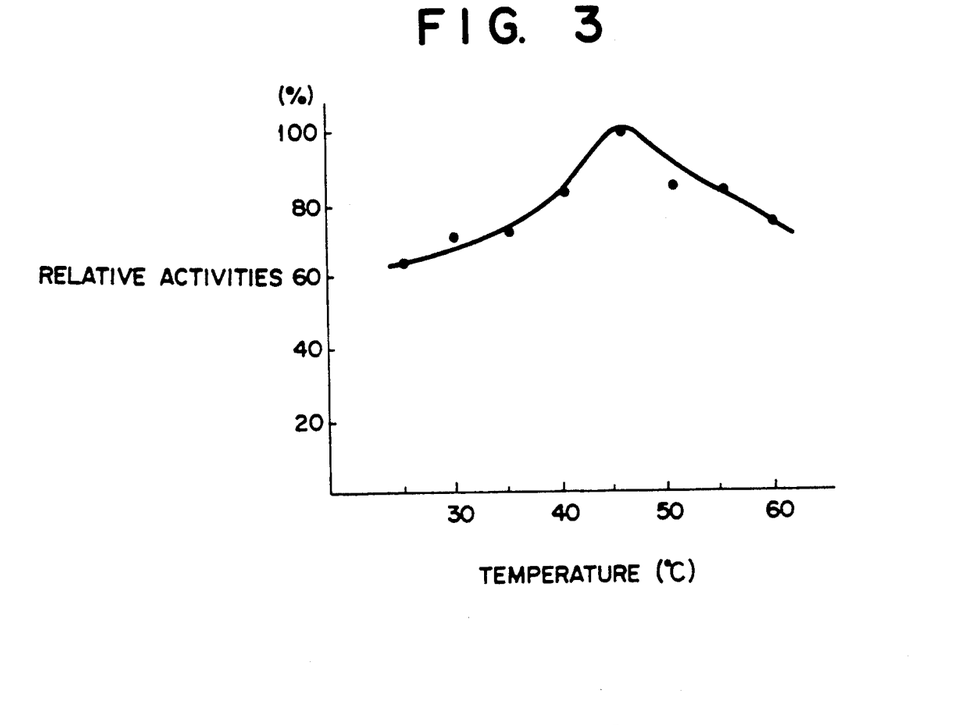
FIG. 3 is a graphic chart showing the optimum acting temperature of that enzyme.

Reaction of the enzyme at various temperatures for 5 minutes in a sodium acetate buffer solution (0.5 mM EDTA) of pH 4.0 showed the relative activities as shown in FIG. 3. Thus, the enzyme acts satisfactorily at from 40° C. to 55° C. at pH 4.0.

(4) Temperature stability

Figure 4:
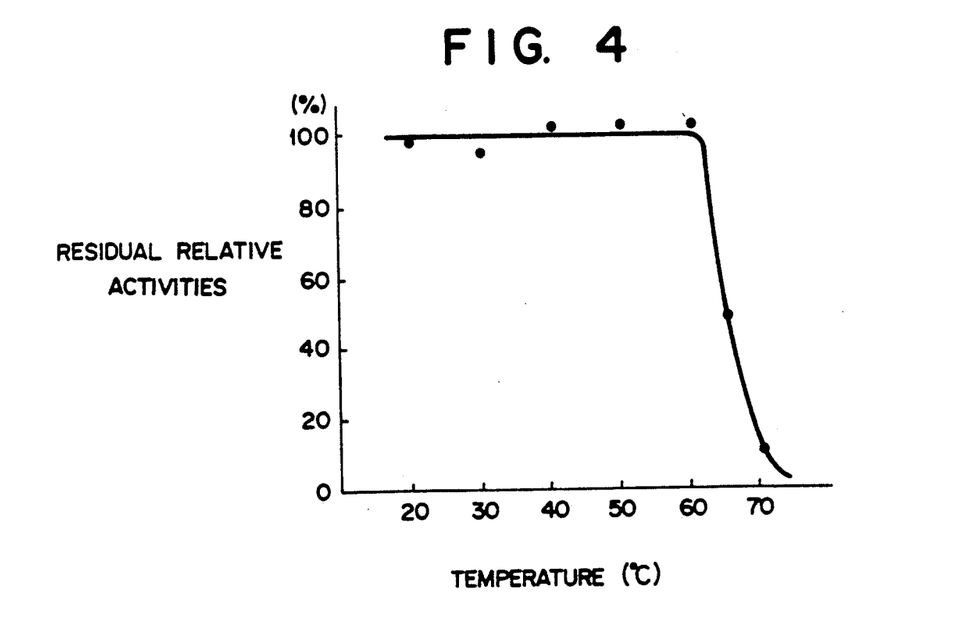
FIG. 4 is a graphic chart showing the temperature stability of that enzyme.

Remaining relative activity after incubation of the enzyme at various temperatures for 30 minutes in a 50 mM phosphate buffer solution (pH 8.0) gave the results as shown in FIG. 4. Thus, the enzyme is stable at below 60° C. under the above conditions.

(5) Molecular weight and subunit structure

Molecular weight of the enzyme is approximately 85,000±5,000 when measured by gel filtration method with a TSK gel G2000 SW Glass column using bovine serum albumin (molecular weight 66,000) and ribonuclease A (originated from bovine pancreas; molecular weight 13,700) as the standard. The enzyme exhibits a single band corresponding to 23,000-2,000 of molecular weight when measured by sodium dodecyl sulfate (SDS)-polyacrylamide gel electrophoresis method using phosphorylase b (originated from rabbit muscle; molecular weight 94,000), bovine serum albumin (molecular weight 67,000), ovalbumin (originated from egg; molecular weight 43,000), carbonic anhydrase (originated from bovine red blood cell; molecular weight 30,000), a trypsin inhibitor (originated from soy beans; molecular weight 20,100), and α-lactoalbumin (originated from cow milk; molecular weight 14,400) as the standard. Thus, the present enzyme is presumed to be a tetramer of the subuit.

(6) Substrate specificity

Substrate specificity as ascorbate oxidases

Oxidations of various enzymes where substrates are phenols or ascorbic acid.

| Substrates | Ascorbate oxidase originated from *Acremonium* sp. HI-25 | Ascorbate oxidase originated from cucumbers | Laccase originated from *Polyporus versicolor* | Polyphenol oxidase originated from mushrooms |
|---|---|---|---|---|
| (Phenols) | | | | |
| Pyrogallol | ∘ | ∘ | x | x |
| 1-Naphthol | ∘ | ∘ | x | x |
| Gallic acid | ∘ | ∘ | x | x |
| Resorcinol | ∘ | ∘ | x | ∘ |
| DL-dopa | ∘ | ∘ | x | x |
| Hydroquinone | ∘ | ∘ | x | x |
| Catechol | ∘ | ∘ | x | x |
| Phloroglucinol | ∘ | ∘ | x | ∘ |
| Ascorbic acid | x | x | x | ∘ |

Notes
x Oxidized
∘ Not oxidized

Ascorbate oxidases orignated from Acremonium sp. HI-25 or cucumbers do not oxidize substrates of phenols but laccase originated from *Polyporus versicolor* or polyphenol oxidase originated from mushrooms do.

(7) Effect of enzyme inhibitors

Residual relative activities after the incubation at 30° C. for 10 minutes together with the following inhibitors in 1 mM concentration are set forth below.

| Inhibitors | residual relative activities (%) |
|---|---|
| control (no addition) | 100 |
| sodium N,N-diethyldithiocarbamate | 101 |
| Na$_2$S | 3 |
| EDTA | 106 |

Thus, the present enzyme is inactivated with sodium sulfide and sodium azide, but not inactivated with sodium N,N-diethyldithiocarbamate and EDTA.

(8) Effect of metallic ions

Effect of various metallic ions in 4.5 mM concentration is as follows.

| Metallic ions (4.5 mM) | metallic salts used | relative residual activities |
|---|---|---|
| control | (no addition) | 100 |
| Mg$^{++}$ | MgCl$_2$.6H$_2$O | 79.2 |
| Co$^{++}$ | CoSO$_4$.7H$_2$O | 108 |
| Ca$^{++}$ | CaCl$_2$.2H$_2$O | 105 |
| Zn$^{++}$ | ZnSO$_4$.7H$_2$O | 100 |
| Mn$^{++}$ | MnSO$_4$.5H$_2$O | 113 |
| Fe$^{++}$ | FeSO$_4$.7H$_2$O | 254 |
| Cu$^{++}$ | CuSO$_4$.5H$_2$O | 29.8 |

As shown in the above, the present enzyme is inactivated by Cu$^{++}$ ions and activated by Fe$^+$ ions.

(8) Isoelectric point

The enzyme shows isoelectric point of 4.0 when measured by isoelectric focusing method.

Above results are compared with the known enzymes as follows.

| Origins | Acremonium sp. HI-25 | Myrothecium verrucaria. hypha | Cucumber |
|---|---|---|---|
| reference | the invention | Nihon Eiyou-Shokuryou Gakukaishi Vol. 40, No. 1 47-51 (1987) | J. Biochem. 64, 189 (1968); Toyobo ASCORBATE OXIDASE catalog No. EC 1.10.3.3 |
| mol. wt. | 80,000 TSKgel G2000 SW) (presumed to be tetramer of 23,000) | 380,000 (Sepharose 6B) (no change in the presence of DTT) | 132,000 (tetramer of 30,000-40,000) |
| isoelectric point | 4.0 | | 6.0-7.8 |
| K m | | 3.0 mM (L-ascorbate) | $2.5 \times 10^{-4}$M (L-ascorbate) |
| optimum pH | 3.5-4.5 | 6-7 (80% active even at 4) | 5.6 |
| optimum temp. | 45° C. (5 minutes reaction | 30° C. (1 hour reaction | 30° C. (5 minutes reaction |
| PH stability | 4-11 | | 7-10 (25° C., 17 hours) |
| temp. stability | below 60° C. (pH 8.0, 30 minutes | below 40° C. | below 40° C. (pH 8.0, 30 minutes effective |
| inhibitors potassium cyanide | | | |
| diethyldithiocarbamate (Na) | no effect | effective (50% at 1 mM) | effective |
| Na₂ S | effective | | effective |
| Phenylthiourea | unmeasurable, absorption at 245 nm | no effect | |
| EDTA | no effect | no effect | |
| D-isoascorbic acid | active | effective (nonantagonistic) | effective |
| metallic ions | activated by $Fe^{2+}$, inhibited by $Cu^{2+}$ (4.5 mM) | activated by $Cu^{2+}$ (0.1 mM) | containing $Cu^{2+}$ |

The present invention provides a method for preventing the oxidative deterioration of foods and drinks through consumption of oxygen by an ascorbate oxidase. In the first embodiment of the present invention, an ascorbate oxidase is added to a food or drink containing a sufficient amount of ascorbic acid, or an ascorbate oxidase together with its substrates, such as ascorbic acid and its salts, and isoascorbic acid and its salts, is added to a food or drink containing no or insufficient amount of ascorbic acid. Thus, oxygen in the food or drink is consumed upon oxidation of the substrate in the food or drink, such as ascorbic acid, with the ascorbate oxidase, whereby the oxidative deterioration of foods and drinks is prevented.

In this method, the enzyme of the present invention, as well as any known enzymes mentioned above, can be employed. In case of acidic drinks, such as fruit fuice, the enzyme of the present invention having the optimum acting pH at acidic range is suitably used, since known enzymes do not well act in acidic range. The amount of the enzyme employed varies depending upon the type of foods and drinks, but it is in general not less than 0.001 unit, preferably not less than 0.02 unit, per gram or milliliter of foods or drinks. More amount of the enzyme causes no problems, but increase of the enzyme amount higher than a certain level does not necessarily increase the preventive effect to the oxidative deterioration.

The amount of ascorbic acid or its salts to be added varies depending upon the type of foods and drinks and the amount of ascorbic acid contained in them naturally, but it is in general 0.01-1.0 weight %, preferably 0.01-0.5 weight %. The salt of ascorbic acid may be its sodium salt, potassium salt, etc. Isoascorbic acid or its salt may be used, instead.

In the second embodiment of the method for preventing the oxidative deterioration of foods and drinks, according to the invention, an oxygen-consuming system is prepared by dissolving an ascorbate oxidase and its substrates, such as ascorbic acid, its salts, isoascorbic acid, and its salts, into an aqueous medium, such as buffer solutions, and a food or drink and the system are filled in a sealed vessel in such a way that the both do not contact each other. Thus, oxygen in the vessel is consumed by the oxygen-consuming system, and the food or drink is deoxygenated. As for the aqueous medium for the oxygen-consuming system, a buffer solution having a pH same or close to the optimum pH of the used enzyme may be employed. For an ascorbate oxidase originated from cucumber, having the optimum acting pH of approximately 5.6, for example, a buffer solution of pH 5-7 is preferably employed. For the enzyme produced by Acremonium strain of the present invention, having the optimum acting pH in acidic range, an acetate buffer solution of pH 4-5, for example, is conveniently employed.

The proportion of the amount of the ascorbate oxidase plus its substrates to the amount of food or drink in the second embodiment is similar to that in the first embodiment. But, it is preferable in the second embodiment to use a little more amount of the enzyme plus its substrate than that in the first embodiment, because it is necessary in the second embodiment to consume, besides oxygen in the food or drink, the environmental oxygen (namely in the vessel).

In working the second embodiment, an enzyme solution and a substrate solution prepared separately may be mixed and filled in a storing vessel containing foods or drinks, and then the vessel may be sealed. But, for efficient deoxygenation of foods or drinks effected through oxygen consumption by the system, it is preferable to fill an enzyme and its substrate in such a way that the both do not react each other, and to allow them to react after sealing the vessel. For that purpose, for example, an enzyme solution and a substrate solution may separately be contained in a storing vessel, and, after sealing, one solution may be poured into another solution. Or, an enzyme solution and a substrate solution may be contained at the both sides of a diaphragm, and, after sealing the vessel, the both solutions may be allowed to mix by destroying the diaphragm. Or, an enzyme and its substrate, one of them being as a solution and the other in the form of powder, may be introduced in a storing vessel, and, after sealing the vessel, the both may be allowed to be mixed. As still another embodiment, a mixture of a powdered enzyme and its powdered substrate, and a liquid medium for enzyme reaction, such as buffer solutions, may be separately introduced to a vessel, and, after sealing, the powdered mixture and the liquid medium may be allowed to be mixed. Moreover, a mixture of a powdered enzyme and its powdered substrates may be wrapped by a membrane which permeates water and oxygen, introduced in a storing vessel, and allowed to contact to foods or drinks when used.

The present invention also provides a deoxygenating agent to be used for a method for preventing the oxidative deterioration of foods and drinks. The deoxygenating agent is characterized by that an ascorbate oxidase and its substrates are contained in a vessel having an opening, or being at least partially constructed with a gas permeable material, in such a way that the enzyme and the substrate do not react each other before use. The vessel of the deoxygenating agent provides an opening or any gas permeable portion, so that environmental air outside the vessel, for example, inside air of a storing vessel for foods and drinks, is consumed when the reaction of the ascorbate oxidase and its substrates begins in the vessel. Various means may be employed so as to keep the enzyme and the substrate not to react before use.

For example, a solution of the enzyme and a solution of the substrate contained in separate containers may be put into a vessel for the deoxygenating agent, so as to allow the solutions to mix together when used, for example, by reversing the vessel. Alternatively, the enzyme solution and the substrate solution may be placed at the both side of a diaphragm in a vessel for the deoxygenating agent, and allowed them to contact each other by destroying the diaphragm when used. As a specific example, a sack made of an easily breakable film or sheet may be used as the diaphragm, which is broken by, for example, a needle material when used. Alternatively, an enzyme and its substrates, one being as a solution and the other in the form of dry powder, may be contained in a vessel for the deoxygenating agent, and allowed them to mix when used. Alternatively, the enzyme and its substrates both in the dried powder state may be contained in an vessel for the deoxygenating agent containing a buffer solution for reaction, and they are allowed to react when used. In such embodiments, powders may be wrapped in a sack made of a film or sheet, and allowed to contact to a buffer solution by breaking the sack by a needle. In case of drinks, a mixture of the powdered enzyme and the powdered substrate may be coated with a film which permeates oxygen and water, and allowed to contact with the drink when used, thereby to accomplish the object.

According to the method of the invention, the oxidative deterioration of foods and drinks can be prevented by deoxygenation of foods and drinks by consuming oxygen through reaction of an ascorbate oxidase with its substrates, such as ascorbic acid, its salts, isoascorbic acid, and its salts. Unlike the case of using glucose oxidase and the like, the present enzyme reaction does not form hydrogen peroxide, thus, foods and drinks are free from contamination with hazardous hydrogen peroxide.

Further, the ascorbate oxidase and its substrates are soluble in aqueous solutions, thus, the appearance of clear foods and drinks is not affected by addition of them.

The enzyme of the present invention produced by the Acremonium strain has the optimum acting pH in acidic range, thus, it is effectively used for preventing the oxidative deterioration of acidic drinks, such as fruit juices.

Thus, the present invention is applied to the prevention of oxidative deterioration of fermented foods and drinks, such as soybean paste (miso), soy sauce, alcoholic drinks, etc., juices, such as orange juice, tomato juice, etc., table luxuries, such as tea, coffee, etc., retort foods, diary products, fatty oils, and other various kinds of foods and drinks.

Now the present invention will more specifically be explained in regard to the working examples.

EXAMPLE 1

Cultivation of Acremonium sp. HI-25 strain

Each 100 ml of a liquid culture medium (pH 6.0) containing 1 % (W/V) of glucose, 1 % (W/V) of polypeptone, 1 % (W/V) of meat extract, 0.1 % (W/V) of dipotassium phosphate, and 0.0001 % (W/V) of magnesium sulfate 7 hydrate, was placed in 180 flasks for shaking culture (500 ml volume each), and sterilized conventionally. After inoculating an Acremonium sp. HI-25 strain, the media were cultivated at 30° C. for 10 days by shaken culture with 7 cm amplitude, 120 rpm. A cultivated medium containing 0.0589 of specific activity (unit per protein, units / A280) of an ascorbate oxidase was obtained.

EXAMPLE 2

Purification of the ascorbate oxidase by Acremonium sp. HI-25

The cultivated medium obtained in Example 1 was filtered by TOYO-ROSHI No. 2 to yield 11.5 liters of a culture filtrate, to which 6.45 kg of ammonium sulfate was added to make it 80 % saturation. After standing in a cooling chamber for effecting precipitation, the supernatant was discarded and the precipitate was collected by centrifugation. The precipitate was suspended in 700 ml of a 20 mM sodium acetatehydrochloric acid buffer solution (pH 5.5) [hereafter referred to as a sodium acetate buffer solution], and the suspension was dialyzed against water overnight. Thereafter, 1 liter of DEAE cellulose equilibrated with the sodium acetate buffer solution was added thereto, and the mixture was subjected to filtration. The resulting precipitate was eluted with 2 liters of the sodium acetate buffer solution containing 0.1M sodium chloride, to obtain an active fraction. The eluate was salted out with ammonium sulfate in 80 % saturation, and the precipitate was separated in similar way as above, which was then suspended in 270 ml of the sodium acetate buffer solution.

Removal of the solid portion left 265 ml of an ascorbate oxidase active fraction.

The enzyme solution was subjected to gel filtration using a Sephacryl S-300 column equilibrated with the sodium acetate buffer solution containing 0.2M sodium chloride, thereby collecting an active fraction, which was then dialyzed overnight against the 20 mM sodium acetate buffer solution (pH 5.0). Thereafter, the enzyme solution was subjected to sodium chloride gradient elution using a DEAE-cellulose column (5×9 cm) equilibrated with the sodium acetate buffer solution, to obtain an active fraction in approximately 0.02–0.08M sodium chloride concentration. The active fraction was concentrated in vacuo to 12 ml, and subjected to gel filtration using a Sephadex G-100 column equilibrated with the sodium acetate buffer solution containing 0.2M sodium chloride, thereby to collect an active fraction, which was then subjected to sodium chloride gradient elution using a TSKgel DEAE-5PW column (5 mm×5 cm) equilibrated with the sodium acetate buffer solution (pH 5.0). Purified ascorbate oxidase was obtained in a fraction at approximately 0.04 was 0.06 sodium chloride concentration. Total protein, total activity, specific activity, and yield in every purification stage are set forth in the following table.

| Variation of activities in every enzymatic purification stage | | | | |
|---|---|---|---|---|
| Purification stage | total protein (A280) | total activity (unit) | specific activity (unit /A280) | Yield (%) |
| culture supernatant | 179,000 | 10,600 | 0.0589 | 100 |
| after ammonium sulfate fractionation | 40,300 | 10,740 | 0.267 | 102 |
| after DEAE-cellulose treatment | 11,100 | 6,690 | 0.603 | 63 |
| after ammonium sulfate fractionation | 8,810 | 6,230 | 0.707 | 59 |
| after Sephacryl S-300 treatment | 1,450 | 5,140 | 3.55 | 49 |
| after DEAE-cellulose treatment | 189 | 3,500 | 18.5 | 33 |
| after Sephadex G-100 treatment | 61.3 | 2,270 | 37.1 | 22 |
| after TSKgel DEAE-5PW treatment | 20.3 | 1,040 | 51.2 | 10 |

EXAMPLE 3

Prevention of oxidative deterioration of tangerine-Valencia orange juice

Using a concentrated and reduced tangenrine-Valencia orange mixture 100 % fruit juice, deoxygenation tests for the enzyme prepared in Example 2 was conducted. Into a dissolved oxygen assaying cell filled with the juice at 25° C., was added 10 μl of an enzyme solution (7.0 units/ml) prepared by dissolving the lyophilized ascorbate oxidase in Example 2 into the 0.1 mol sodium acetate buffer solution (pH 4.0), for deoxygenation. The results are set forth in the following table, in which the results from deoxygenation test using 10 μl of an enzyme solution (23 units/ml, pH 6.0) containing ascorbate oxidase from cucumber (made by Toyobo Co., Ltd.) was also shown. For the dissolved oxygen assay, DO-METER MODEL TD-100 of TOUKOU KAGAKU KENNKYUUSHO was used.

| Deoxygenation of tangerine-Valencia orange juice with ascorbate oxidases (unit: $O_2$ ppm) at 25° C. | | | |
|---|---|---|---|
| Time | 1 tangerine-Valencia orange juice (no enxyme) | 2 tangerine-Valencia orange juice + ascorbate oxidase from cucumber | 3 tangerine-Valencia orange juice + ascorbate oxidase from Acremonium sp. HI-25 |
| start | 3.10 | 2.73 | 1.79 |
| 5 min. | 3.11 | 2.70 | 0.27 |
| 10 min. | 3.10 | 2.71 | 0.02 |
| 15 min. | 3.09 | 2.78 | 0.01 |
| 20 min. | 3.10 | 2.80 | 0.01 |

The tangerine-Valencia orange juice (prepared by CLICO) had a pH of 3.52. While the ascorbate oxidase from cucumber showed little deoxygenation effect at such lower pH value. The ascorbate oxidase from Acremonium sp. HI-25 decreased the oxygen concentration down to 0.01 ppm after 20 minutes.

EXAMPLE 4

Prevention of Deterioration of Milk

Cow milk containing 0.1 % of ascorbic acid dissolved was injected into a dissolved oxygen assaying cell and kept at constant 25° C. To this was injected 50 μl of an enzyme solution (7.0 units/ml) prepared by dissolving the frozen dried ascorbate oxidase in Example 2 into a 0.1 ml phosphate buffer solution (pH 6.0), for deoxygenation. The results are shown in the followint table, in which the results from the deoxygenation test using 50 μl of an enzyme solution (23.0 units/ml, pH 6.0) containing ascorbate oxidase from cucumber having in similar way as above are also shown.

| Deoxygenation of cow milk with ascorbate oxidases (unit: $O_2$ ppm) at 25° C. | | | |
|---|---|---|---|
| Time | 1 ascorbic acid (no enzyme) | 2 ascorbic acid + ascorbate oxidase from cucumber | 3 ascorbic acid + ascorbate oxidase from Acremonium sp. HI-25 |
| start | 7.88 | 7.28 | 7.93 |
| 5 min. | 7.71 | 2.69 | 1.17 |
| 10 min. | 7.60 | 0.61 | 0.04 |
| 15 min. | 7.51 | 0.20 | 0.01 |
| 20 min. | 7.41 | 0.03 | 0.01 |
| 25 min. | 7.33 | 0.01 | — |
| 30 min. | 7.22 | — | — |

Since cow milk has a pH as high as 6.74, even the ascorbate oxidase from cucumber showed similar dissolved oxygen-eliminating effect as in the ascorbate oxidase from Acremonium sp. HI-25.

EXAMPLE 5

Elimination of dissolved oxygen in a pH 4.5 sodium acetate buffer solution with ascorbate oxidases For dissolved oxygen assay, 10 μl of an enzyme solution (7.0 units/ml) prepared by dissolving the lyophilized ascorbate oxidase in Example 2 into the 0.1M sodium acetate buffer solution (pH 4.5) was added to the 0.1M sodium acetate buffer solution containing 0.1 % of ascorbic acid, and kept at 25° C. The results are set forth in the following table, in which the results from the dissolved oxygeneliminating test using 10 μl of an enzyme solution (23 units/ml, pH 6.0) containing ascorbate oxidase from cucumber in similar way as above were also shown.

Elimination of dissolved oxygen with ascorbate oxidas (pH 4.5, 25° C.) (unit: $O_2$ ppm)

| Time | ascorbic acid (no enzyme) | ascorbic acid + ascorbate oxidase from cucumber | ascorbic acid + ascorbate oxidase from Acremonium sp. HI-25 |
|---|---|---|---|
| start | 7.75 | 7.41 | 7.72 |
| 5 min. | 7.34 | 5.95 | 1.37 |
| 10 min. | 7.02 | 5.21 | 0.21 |
| 15 min. | 6.73 | 4.80 | 0.07 |
| 20 min. | 6.48 | 4.52 | 0.02 |

As obvious from the above dissolved oxygen-eliminating test at 25° C. for 20 minutes with ascorbate oxidases at pH 4.5, the ascorbate oxidase from Acremonium sp. HI-25 eliminated oxygen down to 0.02 ppm, while the ascorbate oxidase from cucumber gained merely a 4.52 ppm level.

EXAMPLE 6

Elimination of dissolved oxygen in a pH 6.0 sodium phosphate buffer solution with ascorbate oxidases For dissolved oxygen assay, 10 μl of an enzyme solution (7.0 units/ml) prepared by dissolving the frozen dried ascorbate oxidase in Example 2 into the 0.1M phosphate buffer solution (pH 6.0) was added to the 0.1M sodium phosphate buffer solution (pH 6.0) containing 0.1% ascorbic acid, and kept at 25° C.

The results are shown in the following table, in which the results from the dissolved oxygen assay using 10 μl of an enzyme solution (23 units/ml, pH 6.0) containing ascorbate oxidase from cucumber in similar way as above were also shown.

Elimination of dissolved oxygen with ascorbate oxidases (pH 6.0, 25° C.) (unit: $O_2$ ppm)

| Time | 1 ascorbic acid (no enzyme) | 2 ascorbic acid + ascorbate oxidase from cucumber | 3 ascorbic acid + ascorbate oxidase from Acremonium sp. HI-25 |
|---|---|---|---|
| start | 8.00 | 7.12 | 6.92 |
| 5 min. | 7.38 | 1.88 | 2.45 |
| 10 min. | 6.81 | 0.52 | 0.45 |
| 15 min. | 6.46 | 0.17 | 0.09 |
| 20 min. | 6.10 | 0.08 | 0.02 |

It is obvious from the above table that, at a higher pH range, there is little difference in elimination of dissolved oxygen between the ascorbate oxidase from Acremonium sp. HI-25 and the ascorbate oxidase from cucumber.

EXAMPLE 7

Elimination of oxygen in a vessel with ascorbate oxidases

Five milliliter portion of a solution of 133 mg of ascorbic acid and 8.0 units of the ascorbate oxidase in Example 2 dissolved in a 0.1M sodium phosphate buffer solution (pH 6.0) was added to a sealed 20 ml-volume glass vessel equipped with 39550 OXYGEN ELECTRODE of Beckman OXYGEN ANALYZER, and the amount of oxygen ($O_2$ %) in the glass vessel was measured under constant agitation by a small stirrer. The glass vessel had been kept at a constant temperature controlled to 25°±0.1° C.

The results are set forth in the following table, in which the results from the test for eliminating oxygen in the vessel using 4.7 units of ascorbate oxidase from cucumber with otherwise the similar procedure as of the ascorbate oxidase from Acremonium sp. HI-25 was also shown.

Elimination of oxygen in a vessel with ascorbate oxidases (unit: $O_2$ %) at 25 ± 0.1° C.

| Time | 1 pH 6.0 sodium phosphate buffer solution only | 2 pH 6.0 sodium phosphate buffer solution + ascorbic acid | 3 pH 6.0 sodium phosphate buffer solution + ascorbic acid + ascorbate oxidase from cucumber | 4 pH 6.0 sodium phosphate buffer solution + ascorbic acid + ascorbate oxidase from Acremonium sp. HI-25 |
|---|---|---|---|---|
| start | 20.5 | 20.8 | 21.0 | 20.4 |
| 1 hr. | 20.5 | 20.1 | 15.2 | 17.2 |
| 2 hr. | 20.4 | 19.4 | 11.5 | 14.1 |
| 3 hr. | 20.4 | 18.8 | 9.1 | 11.9 |
| 4 hr. | 20.4 | 18.2 | 7.6 | 10.3 |
| 5 hr. | 20.4 | 17.6 | 6.6 | 9.2 |
| 6 hr. | 20.5 | 17.0 | 6.1 | 7.9 |
| 9 hr. | 20.4 | 15.9 | 5.7 | 5.7 |
| 12 hr. | 20.4 | 14.2 | 5.4 | 4.1 |

As obvious from the above, an enzyme from cucumber eliminates oxygen in the vessel as well as that from Acremonium.

REFERENCE EXAMPLE 1

Ascorbate oxidase activities in the presence of sodium azide

Commonly, $NaN_3$ is used as a preservative agent for test reagents. It has been discovered that the ascorbate oxidase well acts for the reduction of ascorbic acid even in the presence of sodium azide used as a preservative agent together with a drying stabilizer for enzymes, such as BSA, EDTA, etc., as shown in the table below.

Therein, the measuring method of ascorbate oxidase activities was as follows: To each 50 ml of a buffer solution containing 0.1 % of BSA was added ascorbate oxidase. In the NaN3-adding group, $NaN_3$ was added thereto to make its concentration of 0.2%. After 2 days incubation at 5° C. and 28° C., the residual activities were measured, with the results set forth in the following table.

| Origin of enzymes | kind of buffers with or without sodium azide | (unit: %) relative activities. 100 as buffers only | residual activities at 28° C. 100 as 5° C. incubation | residual activities at 28° C. 100 as just after preparation |
|---|---|---|---|---|
| Acremonium | PIPES | 100.0 | 100.0 | 100.0 |

-continued

| Origin of enzymes | kind of buffers with or without sodium azide | relative activities. 100 as buffers only | residual activities. at 28° C. 100 as 5° C. incubation | residual activities at 28° C. 100 as just after preparation |
|---|---|---|---|---|
| cucumber | +NaN₃ | 78.4 | 96.6 | 101.1 |
|  | Pi | 100.0 | 97.6 | 55.6 |
|  | +NaN₃ | 76.2 | 89.5 | 50.5 |
|  | Tris | 100.0 | 101.6 | 68.7 |
|  | +NaN₃ | 78.6 | 88.5 | 64.4 |
|  | PIPES | 100.0 | 103.6 | 76.9 |
|  | +NaN₃ | 89.3 | 88.8 | 71.3 |
|  | Pi | 100.0 | 90.6 | 72.3 |
|  | +NaN₃ | 91.4 | 75.3 | 64.0 |
|  | Tris | 100.0 | 42.6 | 50.0 |
|  | +NaN₃ | 100.0 | 59.5 | 63.8 |

As compared with the values of relative activities of 100 as when using buffer solutions only, the enzyme from Acremonium showed much more decrease in activity caused by NaN₃ than the enzyme from cucumber. But, as seen from the values of relative activities at 28° C. of 100 as 5° C. incubation and that of 100 as just after preparation, it can not be said that the enzyme from Acremonium showed much more decrease in activity caused by NaN₃.

Therein, the ascorbate oxidase activities were measured according to the following method.

Method for measuring activities for reductive consumption of ascorbic acid

A 0.1 ml portion of a 50 mM potassium dihydrogenphosphate-sodium hydroxide buffer solution (pH 5.6) containing 1 mM ascorbic acid and 1 mM disodium ethylenediaminetetraacetate is preliminarily incubated at 37° C. for 5 minutes, and 0.02 ml of an enzyme solution is added thereto. The mixture is allowed to react at 37° C. for accurately 5 minutes, and then the enzyme reaction was stopped by addition of 1.0 ml of a 50 mM potassium dihydrogenphosphate-sodium hydroxide buffer solution (pH 7.6) containing 2 ml nitroblue-tetrazolium (NTB) and 4 % polyoxyethylene (10) octylphenyl ether (Triton X-100). The mixture was stood at 37° C. for 15 minutes to cause reaction of NTB with ascorbic acid. To the resulting reaction mixture was added 2.5 ml of 0.1M hydrochloric acid containing 0.1 % Triton X-100, and the absorbance at 530 nm was measured. The activity is calculated from the difference of absorbance of the reaction mixture using no enzyme.

REFERENCE EXAMPLE 2

Comparison of stabilities of ascorbate oxidases

Comparative stability tests were conducted with the ascorbate oxidase from Acremonium sp. HI-25 (A. ASOD) and a conventional ascorbate oxidase from cucumber (C. ASOD) produced by AMANO SEIYAKU.

After removal of microorganism by 0.2 μm membrane filter, A. ASOD or C. ASOD is added to a given amount of sterilized 50 mM phosphate buffer solution (pH 6.0 and 6.85), and stored at 4° C. or 30° C. for 3 days.

The results are as follows.

| | | | | (residual activity: u/ml) | | | |
|---|---|---|---|---|---|---|---|
| Lot No. | storing temp. | pH | enzymes | start | 1st day | 2nd day | 3rd day |
| 1 | 30° C. | 6.0 | A.ASOD | 0.345 | 0.337 | 0.345 | 0.384 |
|  | 30° C. | 6.0 | C.ASOD | 0.482 | 0.057 | 0.034 | 0.022 |
| 2 | 30° C. | 6.85 | A.ASOD | 0.263 | 0.216 | 0.248 | 0.238 |
|  | 30° C. | 6.85 | C.ASOD | 0.351 | 0.127 | 0.096 | 0.044 |
| Lot No. | storing temp. | pH | enzymes | start | 6th day | 14th day | 20th day |
| 3 | 4° C. | 6.0 | A.ASOD | 0.345 | 0.396 | 0.352 | 0.323 |
|  | 4° C. | 6.0 | C.ASOD | 0.622 | 0.202 | 0.181 | 0.113 |
| 4 | 4° C. | 6.85 | A.ASOD | 0.263 | 0.256 | 0.268 | 0.295 |
|  | 4° C. | 6.85 | C.ASOD | 0.561 | 0.214 | 0.102 | 0.079 |

Therein, the activities of ascorbate oxidases were measured according to the method mentioned in "Measurement of enzyme activities" in the text. The above results show that the ascorbate oxidase from Acremonium (A. ASOD) exhibits higher residual activity and stability in every lots, as compared with the ascorbate oxidase from cucumber (C. ASOD).

REFERENCE EXAMPLE 3

Measurement of phospholipid in blood serum

To measure phospholipid in blood serum, in general, a sample is incubated with phospholipase D to form choline, and the choline is oxydized with choline oxidase to form hydrogen peroxide. The hydrogen peroxide is oxidized with peroxidase, whereby a chromogen is allowed to develop by oxidation with the generating oxygen, thereby to measure phospholipid. In this measurement, ascorbic acid in the sample hinders the accurate quantitation of phospholipid because it inhibits the peroxidase reaction by involving to the color development. To avoid such troubles, ascorbate oxidases are employed.

Heretofore, ascorbate oxidase from cucumber has been used for such purpose. As set forth in the above stability tests, however, the enzyme from cucumber is not fully satisfactory in its stability, and is not able to store for long time after the preparation of reagents, that being inconvenient, causing any loss, thus expensive. These problems will be dissolved by use of the ascorbate oxidase from Acremonium.

Preparation of "Merck-type reagent solution-1"

Phospholipase D (PLD) [a bottle of Merck enzyme reagent 1 (77037)] and an ascorbate oxidase [a bottle of Merck 77049] are dissolved in 100 ml of 0.5 mmol 3,5-di-methoxy-N-ethyl-N-(2-hydroxy-3-sulfopropyl)-aniline [a bottle of Merck buffer solution-1 (77038)].

Preparation of "Acremo-type reagent solution-1"

Phospholipase D (PLD) [a bottle of Merck enzyme reagent-1 (77037)] and 150 units of ascorbate oxidase from Acremonium are dissolved in 100 ml of 3,5-dimethoxy-N-ethyl-N-(2-hydroxy-3-sulfopropyl)aniline [a bottle of Merck buffer solution-1 (770389)].

Using these reagent solutions, phospholipid in human blood serum samples was measured, with the results set forth in the following table.

| | Sample | blank | sample | blank |
|---|---|---|---|---|
| reagent solution-1 | 2.0 ml | 2.0 ml | — | — |

|  | Sample | blank | sample | blank |
|---|---|---|---|---|
| (Merck-type) reagent solution-1 | — | — | 2.0 ml | 2.0 ml |
| (Acremo-type) sample | 0.025 ml | — | 0.025 ml | — |
| | admixed and incubated at 37° C. for 3 minutes | | | |
| reagent solution-2 | 2.0 ml | 2.0 ml | 2.0 ml | 2.0 ml |
| | admixed and incubated at 37° C. for 5 minutes. then samples measured against blanks | | | |
| results measured (600 nm) | 0.232 | control | 0.236 | control |

Although the values have not been converted to the real phospholipid amounts in human blood serum, it is found from the table that the value obtained by use of ascorbate oxidase from Acremonium is comparable with that from cucumber.

Besides the measurement of phospholipid, the enzyme may be utilized in testing agents where ascorbate oxidase is used, such as for measurements of cholesterol, triglycerides, uric acid, free fatty acids, etc.

REFERENCE EXAMPLE 4

Measurement of ascorbic acid by an enzyme sensor

Figure 5:
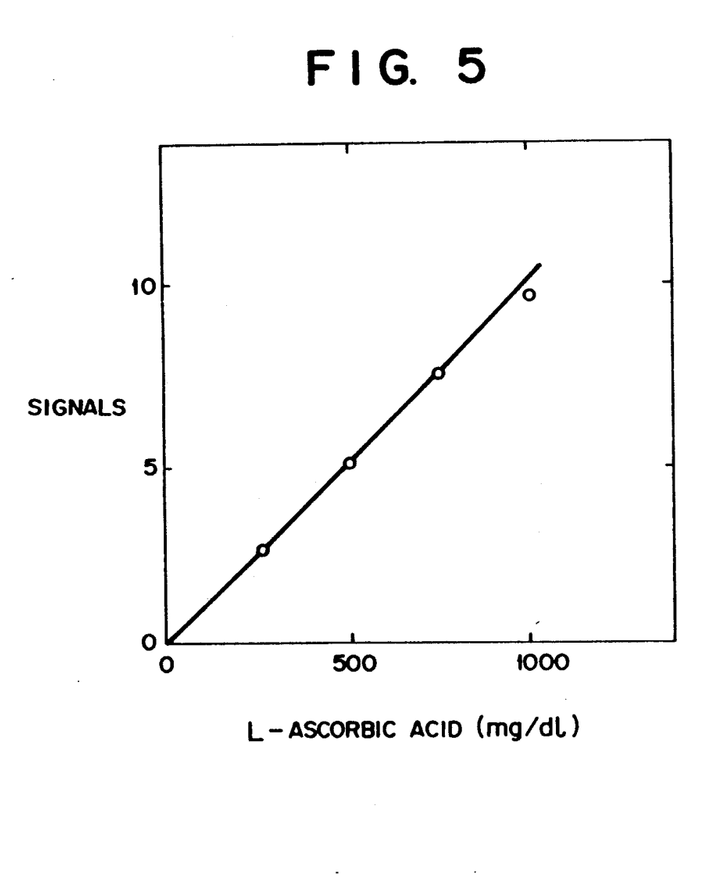
FIG. 5 is a graphic chart showing a standard curve for L-ascorbic acid using cucumber-originated ascorbate oxidase.
Figure 6:
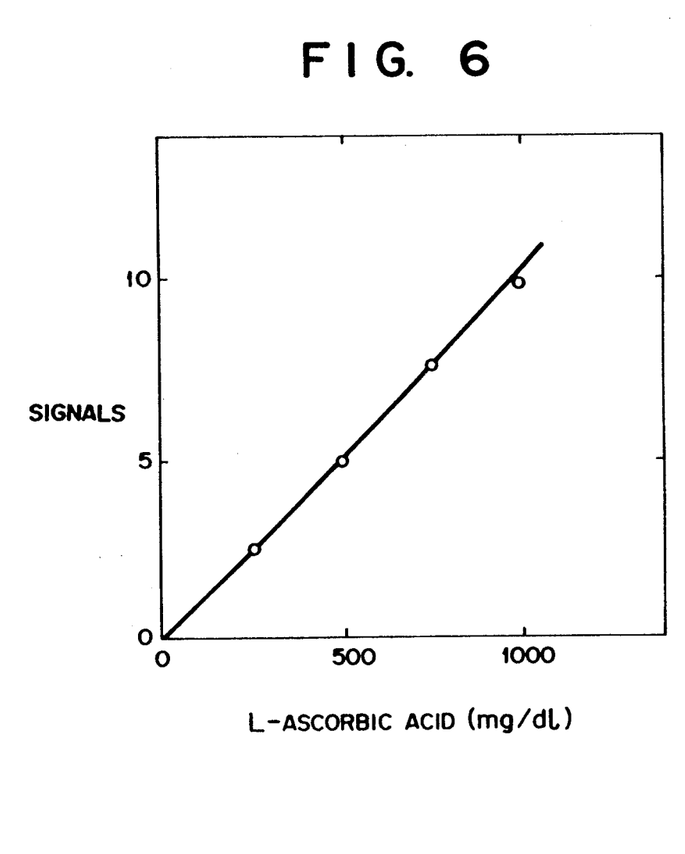
FIG. 6 is a graphic chart showing a standard curve for L-assorbic acid using Acremonium-originated ascorbate oxidase.

Ten sheets of aminated polyacrylonitrile (PAN) membrane (1.5 cm square) were put into a 5 ml of a 12.5 % glutaraldehyde solution, and allowed to react at 0° C. for 20 minutes. Then, the membranes were rinsed with 500 ml of 0.1M borate buffer solution (pH 8.5), and added with cucumber originated or present ascorbate oxidase (1200 units) dissolved in 10 ml of a 0.1M phosphate buffer solution (pH 7.5). The mass was allowed to react at 30° C. for 1 hour to secure immobilization of the enzyme onto the membrane. After rinsed with a 0.1M phosphate buffer solution (pH 7.5), the enzyme-immobilized membranes were mounted onto oxygen electrodes for measurement of ascorbic acid. To measure ascorbic acid, 30 μl of an ascorbic acid-containing solution was added to 1.5 ml of an 0.1M phosphate buffer solution, and the decrease of amount of dissolved oxygen was measured. The results are shown in FIG. 5 (an enzyme from cucumber) and FIG. 6 (an enzyme from Acremonium).

REFERENCE EXAMPLE 5

Figure 7:
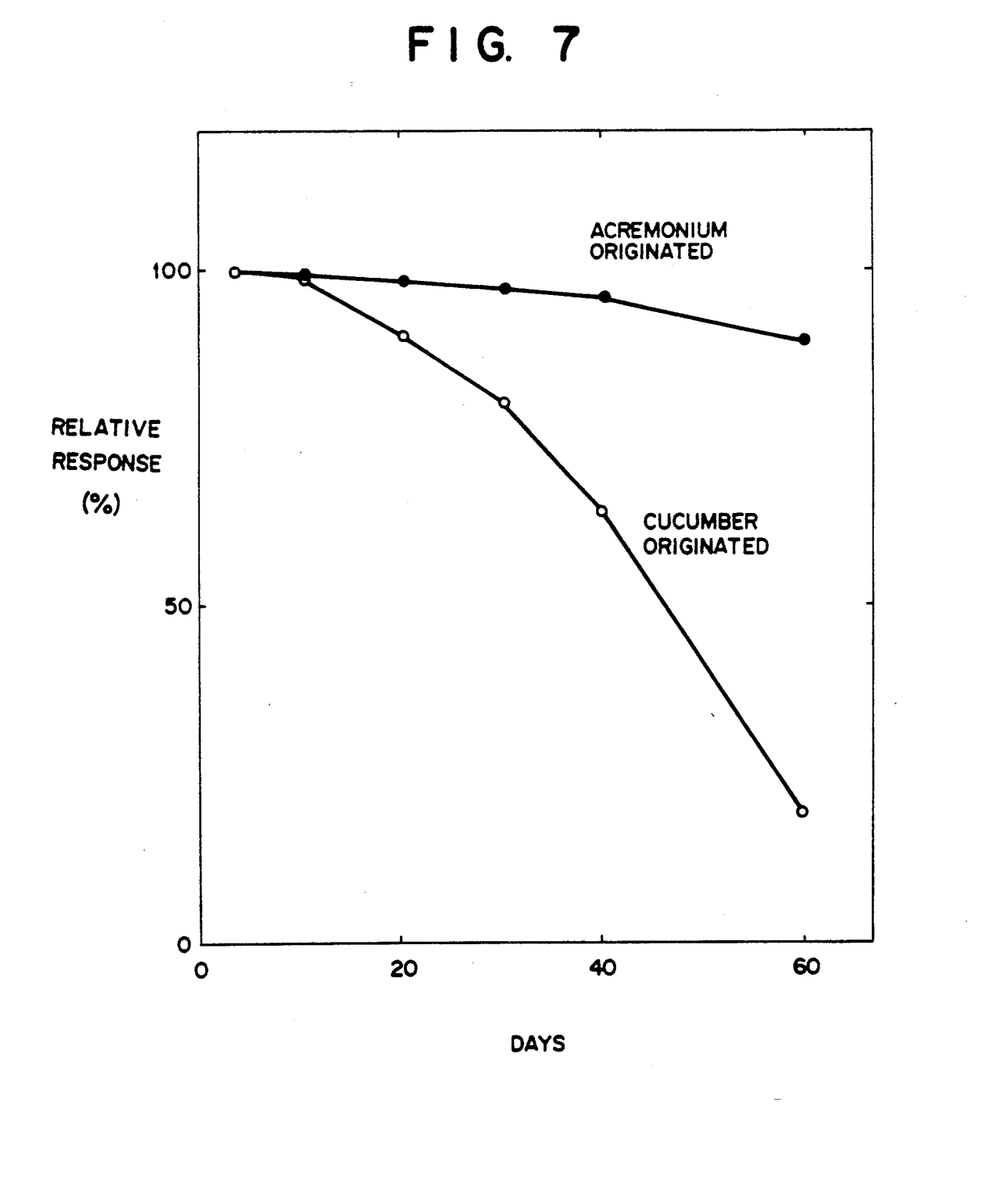
FIG. 7 is a graphic chart showing enzyme stability of immobilized ascorbate oxidase.

These two kinds of enzyme-immobilized membranes were stored in a 0.1M phosphate buffer solution (pH 7.5) at 37° C., and used for the measurement of ascorbic acid from time to time. As obvious from FIG. 7, the enzyme from Acremonium shows superior stability to the enzyme from cucumber.

We claim:

1. An isolated ascorbate oxidase having the properties as mentioned below:
   (1) having a pH optimum in the range of pH 3.5-4.5;
   (2) being activated by $Fe^{++}$ and inhibited by $Cu^{++}$;
   (3) having a molecular weight of 85,000±5,000 as determined by the gel filtration method, and subunit molecular weight of 23,000+2,000 as determined by the sodium dodecyl sulfate/polyacrylamide gel electrophoresis method;
   (4) having an isoelectric point of pI 4.0 as measured by the isoelectric focusing method;
   (5) showing stable activity at pH 8.0 when heated to a temperature as high as 60° C. for 30 minutes; and
   (6) showing stable activity at 4° C. over the pH range of pH 4-11.

* * * * *